(12) United States Patent
Rossier et al.

(10) Patent No.: US 7,037,417 B2
(45) Date of Patent: May 2, 2006

(54) MECHANICAL CONTROL OF FLUIDS IN MICRO-ANALYTICAL DEVICES

(75) Inventors: Joel S. Rossier, Aigle (CH); Frederic Reymond, La Conversion (CH); Hye Jin Lee, Madison, WI (US); Xiaoxia Bai, Lausanne (CH); Hubert H. Girault, Ropraz (CH)

(73) Assignees: Ecole Polytechnique Federale de Lausanne, Lausanne (CH); DiagnoSwiss SA, Monthey (CH)

( * ) Notice: Subject to any disclaimer, the term of this patent is extended or adjusted under 35 U.S.C. 154(b) by 776 days.

(21) Appl. No.: 09/812,065

(22) Filed: Mar. 19, 2001

(65) Prior Publication Data

US 2002/0130044 A1 Sep. 19, 2002

(51) Int. Cl.
*G01N 27/26* (2006.01)

(52) U.S. Cl. .................. 204/453; 204/451; 204/452; 204/601; 204/603; 204/604; 137/625; 137/862; 422/70; 422/103

(58) Field of Classification Search ................ 204/450, 204/451, 452, 453, 600, 603, 604, 601; 137/625, 137/862; 422/70, 100, 103
See application file for complete search history.

(56) References Cited

U.S. PATENT DOCUMENTS

| 5,389,221 | A | * | 2/1995 | Jorgenson et al. .......... 204/603 |
| 5,858,195 | A | | 1/1999 | Ramsey |
| 6,001,229 | A | | 12/1999 | Ramsey |
| 6,010,607 | A | | 1/2000 | Ramsey |
| 6,010,608 | A | | 1/2000 | Ramsey |
| 6,033,546 | A | | 3/2000 | Ramsey |
| 6,235,471 | B1 | * | 5/2001 | Knapp et al. .................. 435/6 |
| 6,315,952 | B1 | * | 11/2001 | Sklar et al. .................... 422/63 |
| 6,375,817 | B1 | * | 4/2002 | Taylor et al. ................ 204/453 |
| 6,458,259 | B1 | * | 10/2002 | Parce et al. ................. 204/454 |
| 2001/0052460 | A1 | * | 12/2001 | Chien et al. ................ 204/450 |
| 2002/0166592 | A1 | * | 11/2002 | Liu et al. .................... 137/825 |

* cited by examiner

*Primary Examiner*—Nam Nguyen
*Assistant Examiner*—Brian L Mutschler
(74) *Attorney, Agent, or Firm*—Howson and Howson

(57) ABSTRACT

An apparatus for manipulating fluid samples comprises a micro-chip device having first and second covered channels, each channel having openings at both ends. The channels intersect to form a common intersection. Three of the openings of the channels are connected to a multi-port valve to control pressure in the device.

20 Claims, 11 Drawing Sheets

MECHANICAL CONTROL OF FLUIDS IN MICRO-ANALYTICAL DEVICES

FIELD OF THE INVENTION

This invention relates to an apparatus and method for manipulating fluid samples.

BACKGROUND TO THE INVENTION

Miniaturization of analytical systems has played an important role in the development of fast analysis systems using very small amounts of sample. During the last decade, intensive efforts have been devoted to the design of whole laboratory systems on micro-analytical substrates as analytical tools, utilising for example, capillary electrophoresis and liquid chromatography. However, developments in microanalysis have been hindered to some extent by the lack of efficient fluid pumping systems. Fluid movement in micro-channel networks formed in glass, silica or polymeric substrates is conventionally driven by capillary flow or electro-osmotic pumping. The former process relies on chemical modifications of the surface properties of the micro-analytical substrate, which in turn establish restrictions on the flow direction and rate. The latter process involves high-voltage inputs through electrodes in contact with a solution, which is usually referred to as electrokinetic pumping.

A critical parameter in performing high-resolution electrophoresis or electrochromatography is the injection. In standard capillary electrophoresis two injection methods are generally used. The first method, electrokinetic injection, is easy to perform and requires placing the capillary in contact with a sample solution and pumping the latter inside the capillary by applying a high voltage. However, this injection method is not always suitable as in the case where some of the species in the sample to be analysed have very different electrophoretic mobilities. In this case some of the species will migrate during the injection, resulting in bias in the final concentration ratio between the analytes. For instance, the injection of a sample in pure water in order to generate a strong stacking effect is very difficult using this method. Also, the injection of very complex mixtures, for example samples of high protein concentration, is difficult, because the proteins may change the zeta potential in the sample channel resulting in instability in the flow intensity or even in the electro-osmotic flow direction. Several injection patterns based on electrically driven flow have been proposed such as T-injection, double-T-injection as well as electrically pinched injection as exemplified in U.S. Pat. Nos. 5,858,195; 6,001,229; 6,010,607; 6,010,608; and 6,033,546. All of these inventions were linked to the application of a high voltage facilitating pumping of the sample solution. Several potentials can be applied in different channels of the device in order to force the solution to flow producing well defined sample plugs. The principal drawback of the inventions described is the necessity to work with samples which have well-defined conductivity, viscosity and thermal properties. Therefore, analyses of other samples has to be performed using the second method of injection, pressure driven injection, which is less sensitive to sample composition.

SUMMARY OF THE INVENTION

The present invention relates to an apparatus and method of use thereof for performing fluid manipulations in micro-analytical laboratory systems for a large variety of applications, including sample injection. The invention allows precise control of fluid transport in micro-fabricated systems for performing chemical and biochemical analyses, syntheses and detection.

The method of the invention combines a multi-port valve to control the pressure in a network of micro-channels with mechanical pumping of a fluid to provide low cost analytical devices that can be coupled to conventional separation and/or detection systems that find broad applications in the fields of chemistry, biochemistry, biotechnology, molecular biology and numerous other fields.

The system can be used as a pressure injector facilitating separation by means of chromatography, electrophoresis or electrochromatography in micro-analytical systems. The present invention comprises a new method for pumping, injecting and driving fluids by employing a multi-port injection valve to control the pressure in portions of a micro-channel network and a mechanical pump to introduce fluids in said portions.

The device is composed of interconnected covered channels connected with tubes to an external multi-port injection valve. The multi-port injection valve controls the direction of the flow within the different sections of the device. The system can be used to prepare a sample plug by pressure to perform chromatography, electrochromatography and/or electrophoresis. The sample solution can be an aqueous or an organic solution, and can contain dissolved species such as one or more salts. The invention is not limited by the concentration, conductivity or thermal properties of the sample.

The present invention relates to a micro-analytical apparatus for manipulating fluid samples, comprising a substrate having at least a first and second covered channel with openings at either end of said first and second channel, said first and second covered channels intersecting to form a common intersection, characterized in that at least three of the openings to said first and second covered channels are connected to a multi-port valve to control the pressure in the channels.

The substrate of the invention is preferably made of a substance selected from the following materials: glass, silicon, ceramic, organic polymers, a metallic material or mixtures thereof. Other suitable substances will be apparent to those skilled in the art.

Preferably, the channels in the substrate are covered by lamination, thermal bonding, anodic bonding, electrostatic interaction, pressure or a combination thereof.

In an embodiment of the invention all of the openings at either end of the first and second covered channels are connected to the multi-port valve.

In a further embodiment of the invention the first or second covered channel contains a detection region.

In a preferred embodiment of the invention the detection region consists of electrodes, or a window for spectroscopic detection.

In an alternative embodiment of the invention the first or second covered channel is connected to a detection device.

The apparatus according to the present invention can be used in a method of manipulating fluid samples by:

a. mechanically pumping an eluent solution into one end of the first covered channel and through the intersection whilst applying pressure to either end of the second covered channel when the multi-port valve is in a first position;

b. then switching the multi-port valve to a second position so that a sample solution is pumped into one end of the second covered channel whilst pressure is applied at the other three openings; and c. switching the multi-port valve back to the first position so that the sample is pushed from one arm of the second covered channel of the device into the intersection and along the first channel.

Alternatively, the apparatus of the invention can be employed when an electrical field is applied in a portion of said first or second channel in order to sustain or stop the flow of liquid during the injection step.

In an alternative embodiment of the method of the invention pressure is applied only during the injection step.

In a still further embodiment of the invention the sample is pushed from one arm of the second covered channel into the intersection and along the first covered channel of the device by means of electrophoresis, electro-osmosis or the like.

Alternatively, at least part of the first or second covered channel contains a stationary phase in order to perform chromatography, electrochemistry, electrophoresis, immunological or enzymatic analysis or any combination thereof.

The term stationary phase refers to any chemical or biological compound immobilized (for instance by physi- or chemi-sorption, by ionic or covalent binding) onto a wall of said covered micro-channel or onto the surface of a packing material like beads filling said covered micro-channel.

BRIEF DESCRIPTION OF THE DRAWINGS

The invention will now be described in more detail, by way of example only, with reference to the accompanying drawings, in which.

DETAILED DESCRIPTION OF THE INVENTION

EXAMPLE 1

Figure 1:
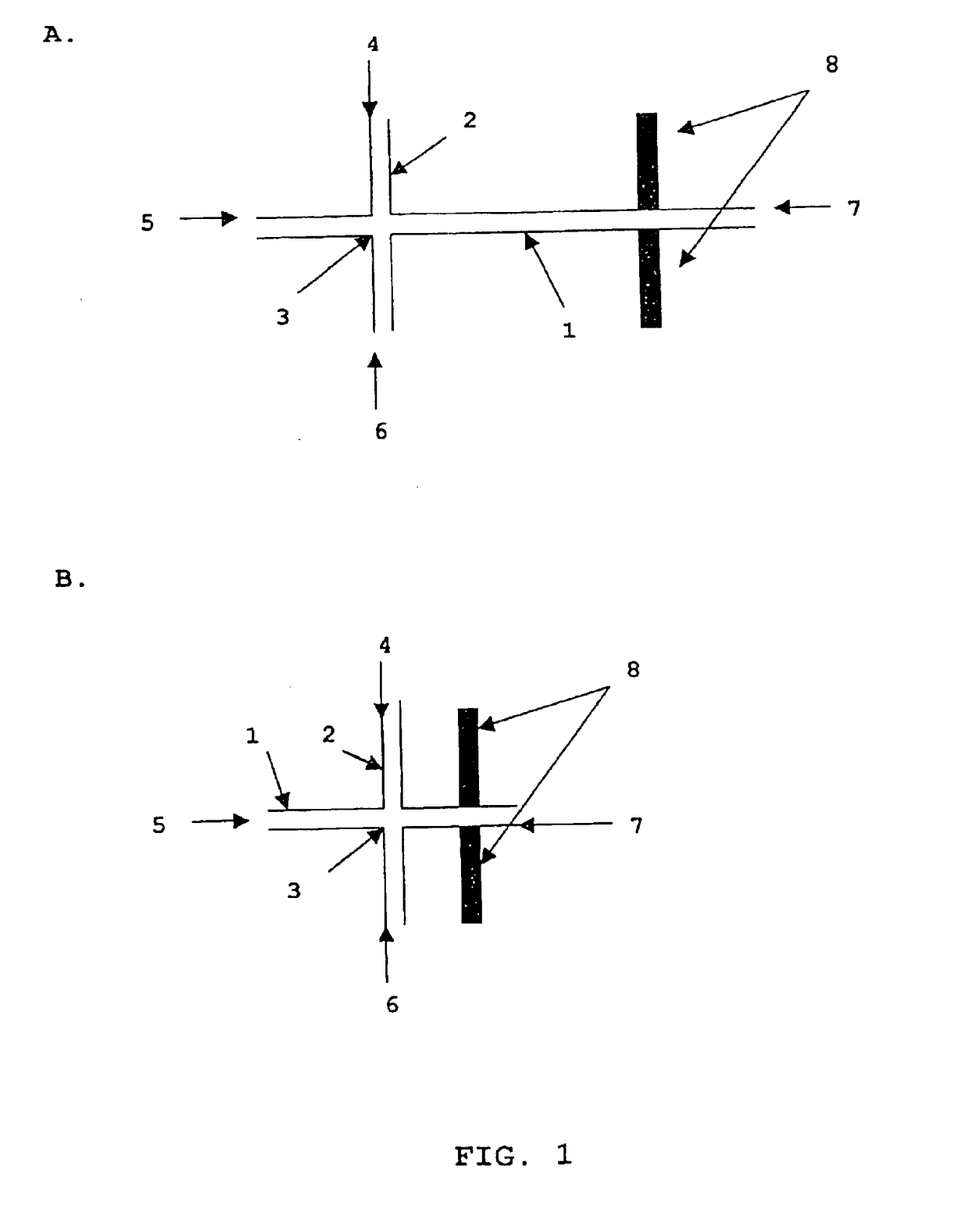
FIGS. 1(a) and 1(b) are schematic diagrams of a polymer micro-analytical device according to two alternative embodiments of the invention.

A micro-channel network on a polymer substrate (e.g. polyethylene terephthalate (PET)) was fabricated by the use of UV Excimer laser photoablation. A schematic diagram of the analytical micro-analytical device is shown in FIG. 1. The device comprises an injector, a separation column and a detector 8. The injection part is composed of an intersection 3 between two side micro-channels 1, 2 perpendicularly photoablated to the main channel. The channels are then covered by lamination forming a set of capillaries.

The structure shown in FIG. 1(a) is composed of an assymetrical cross of covered microchannels 1, 2 that can be connected to external tubes at positions 4, 5, 6 and 7. In the longer channel 1 (5 cm), a conductivity detector 8 can be inserted to detect the injected plugs. The structure shown in FIG. 1(b) comprises four symmetrical arms of equal length (1.1 cm) that can contain electrodes 8 for detection or for voltage application purposes. The arms extend from intersection 3 respectively to openings at positions 4, 5, 6, and 7, and may thus be referred to for convenience as arms 4-3, 5-3, 6-3, and 7-3. Arms will be designated in a similar manner subsequently in this specification.

EXAMPLE 2

Simple Switch

Figure 2A:
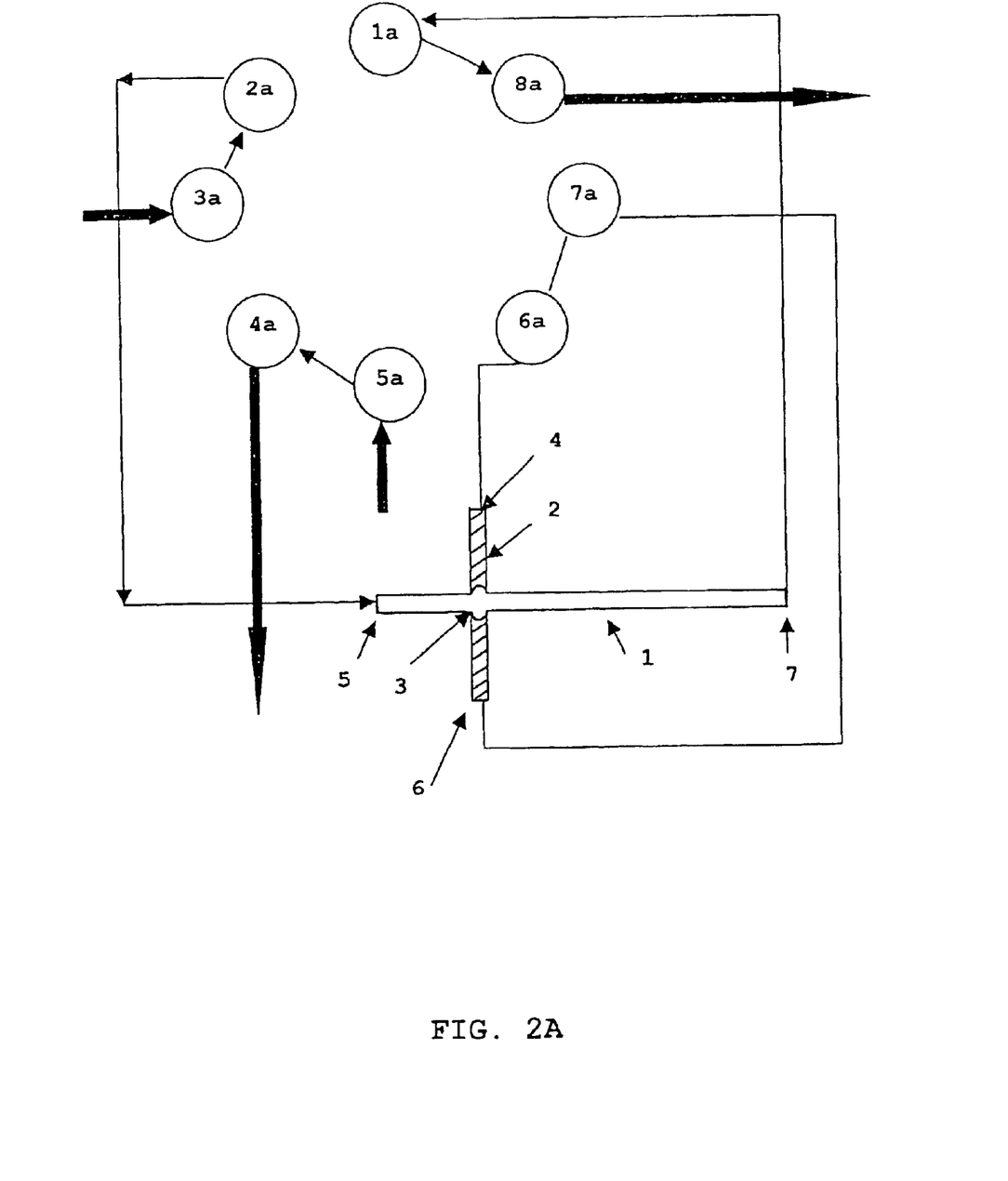
FIGS. 2(a), (b) and (c) are schematic diagrams of a two-way micro-8-port valve connected to a micro-channel network similar to that shown in FIG. 1.
Figure 2B:
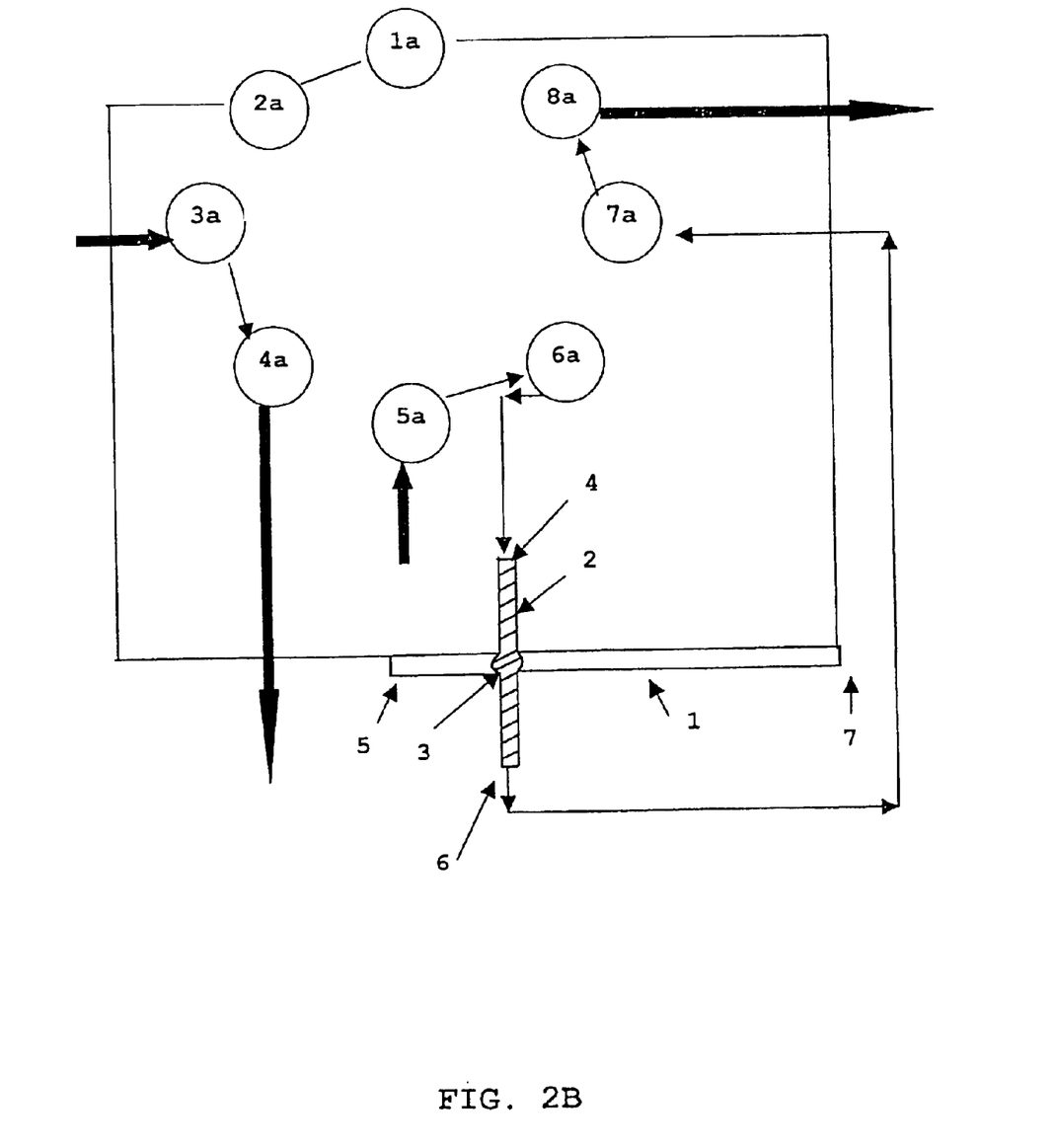
Figure 2C:
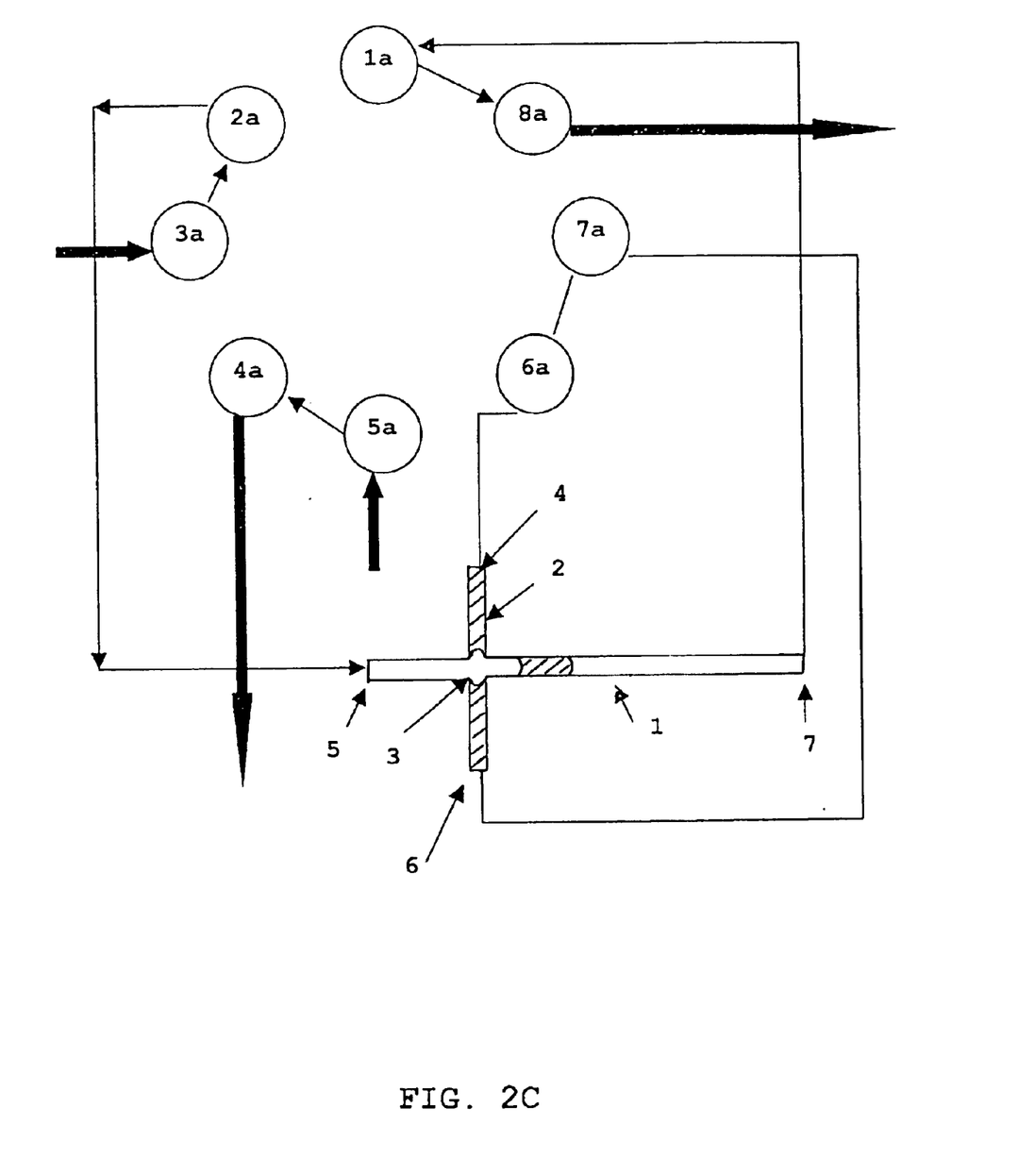

FIGS. 2(a), (b) and (c) illustrate how a sample can be injected in a micro-channel network of the present invention.

Four inlet reservoirs of the micro-channel network, at positions 4, 5, 6 and 7, were connected to a two-way micro-8-port valve with the configuration shown in FIG. 2(a) allowing injection and elution of the sample. The 8-port micro-valve was connected to syringe pumps with a flow rate range of between 0.01 to 1000 $\mu l \cdot h^{-1}$ which are connected to the micro-channel.

The first method necessitates the use of two solutions (running buffer and sample solution) that are pumped independently inside the structure. On one position of the valve (see FIG. 2 (a) the running buffer is pumped from one opening at position 5, which serves as an inlet, to one opening at position 7, which serves as an outlet, whereas both side arms 4-3 and 6-3 i.e., the arm extending from intersection 3 to the opening at position 4 and the arm extending from intersection 3 to the opening at position 6, are connected together as a loop. In this case, the running solution is pumped linearly throughout the structure. At a given time, the multiport valve is switched to the second position represented by FIG. 2 (b), where the sample enters from side arm 4-3, whereas this time no flow is entering the main channel 1. During this time, a plug is formed at the intersection 3. The multiport valve is then placed on the first position (FIG. 2a), where the running buffer drives the sample in the intersection 3 into the main channel 1 towards the outlet opening at position 7 or a detector.

FIGS. 2(a), (b) and (c) are schematic diagrams showing a two-way micro-8-port valve connected to a micro-channel network similar to those shown in FIG. 1, which defines the movement of a sample and an elution solution as a function of the position of the valve. FIGS. 2(a), (b) and (c) illustrate how a sample can be injected into the micro-channel network of the invention.

A) The micro-8-port valve is put into Position A, which corresponds to port 1a connected to port 8a, 2a to 3a, 4a to 5a, and 6a to 7a. In this configuration, the eluent flows from port 2a into the main channel 1 and then out to port 1a, whereas the sample does not flow within the micro-channel network; the pressure is maintained constant in the sample branch 2 of the micro-channel network since the loop of ports 6a and 7a is closed.

B) Then the micro-8-port valve is put into Position B which corresponds to port 1a connected to port 2a, 3a to 4a, 5a to 6a, and 7a to 8a. In this configuration, the eluent does not flow within the micro-channel network, whereas the sample solution flows from port 6a into the sample channel 2 and then out to port 7a. The pressure is maintained constant in the main channel 1 of the micro-channel network since the loop of ports 1a and 2a is closed. During this procedure a plug is formed at the intersection.

C) The micro-8-port valve is then put back to Position A. As a result, the eluent pushes the sample plug into the main channel 1 towards the channel outlet at position 7 or a detector 8.

It is clear from the arrangement described in A and C above that the connections between ports 1a and 2a and the connection between ports 6a and 7a can be blocked without affecting the injection and separation pattern.

Figure 3:
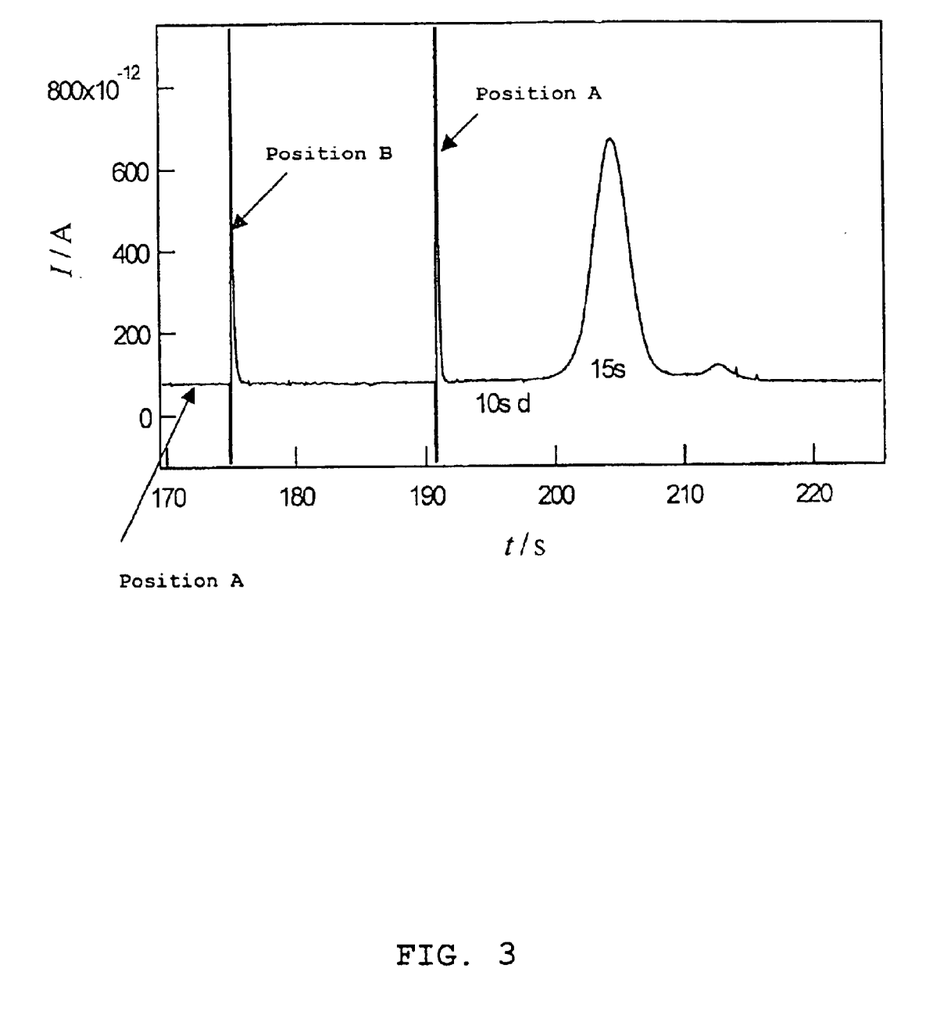
FIG. 3 is a chromatogram obtained by amperometric measurement following injection of hexacyanoferrate into the apparatus shown in FIG. 2.
Figure 4:
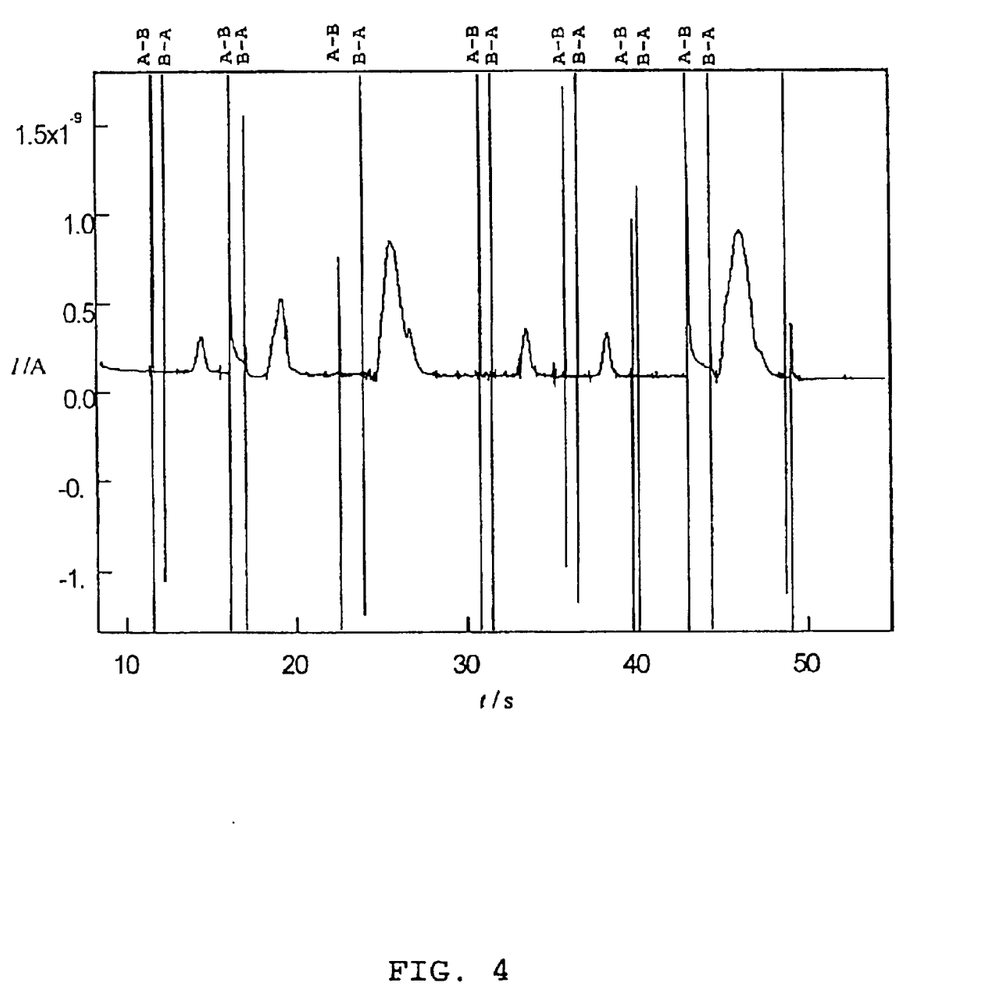
FIG. 4 is a chromatogram showing the results of the reproducibility test of the injection in the configuration presented in FIG. 2.

To illustrate the simple switch method experimental data relating to the oxidation of 10 mM of hexacyanoferrate measured by amperometric detection are shown in FIG. 3. (800 mV was applied between two electrodes placed facing each other in the microchannel). The sharp lines on the chromatogram occur as a result of the switch of the multiport valve from position A to position B. The simple switch method allows very accurate control of the injection or of the separation sequences. In this example the injected peak reached the detector about 10 seconds after the switch, whereas the plug was formed in about 15 seconds. The shape of the detected peak is Gaussian which indicates convective flow of the solution. In order to test the reproducibility of the injection pattern, other experiments were performed by varying the injection time. The results obtained from these experiments are shown in FIG. 4 where A-B indicates the switch from position A to position B of the microport valve and B-A indicates the switch from position B to position A of the microport valve. These results indicate that the shape and the retention time of the injected plug depend on the injection time. This irreproducibility is probably due to sample diffusion or compression along the main channel, meaning that the sample plug will not be well controlled under such conditions. However, such variations can be resolved by controlling the flow rate in the connection tubes by for example connecting them to tubes or capillaries of different dimensions or working with different flow rates.

EXAMPLE 3

Pressure Pinched Switch

In order to eliminate the time dependence of the sample plug size during the injection, it is possible to force running buffer along both sides of the sample flow. This system is similar to the pinched injection method invented by Ramsey and described in U.S. Pat. No. 6,033,546, which is controlled by electrically driven flow for performing microfluidic manipulation. Indeed, in both cases, the sample solution is pumped through the intersection whilst two concurrent flows are pinching it from the side. This means that the sample solution has no time to diffuse inside the main channel and the injection plug volume is independent of the duration of the injection. The fundamental difference of the present invention is that no electrical field is necessary inside the structure in order to pump the solution. Therefore, the present device can be used for the manipulation of solutions that do not contain salt or contain very complex mixtures of solute molecules, including high concentrations of charged species. To achieve this goal, the tubes must be connected in a different way to the structure through the multi-port valve.

Figure 5A:
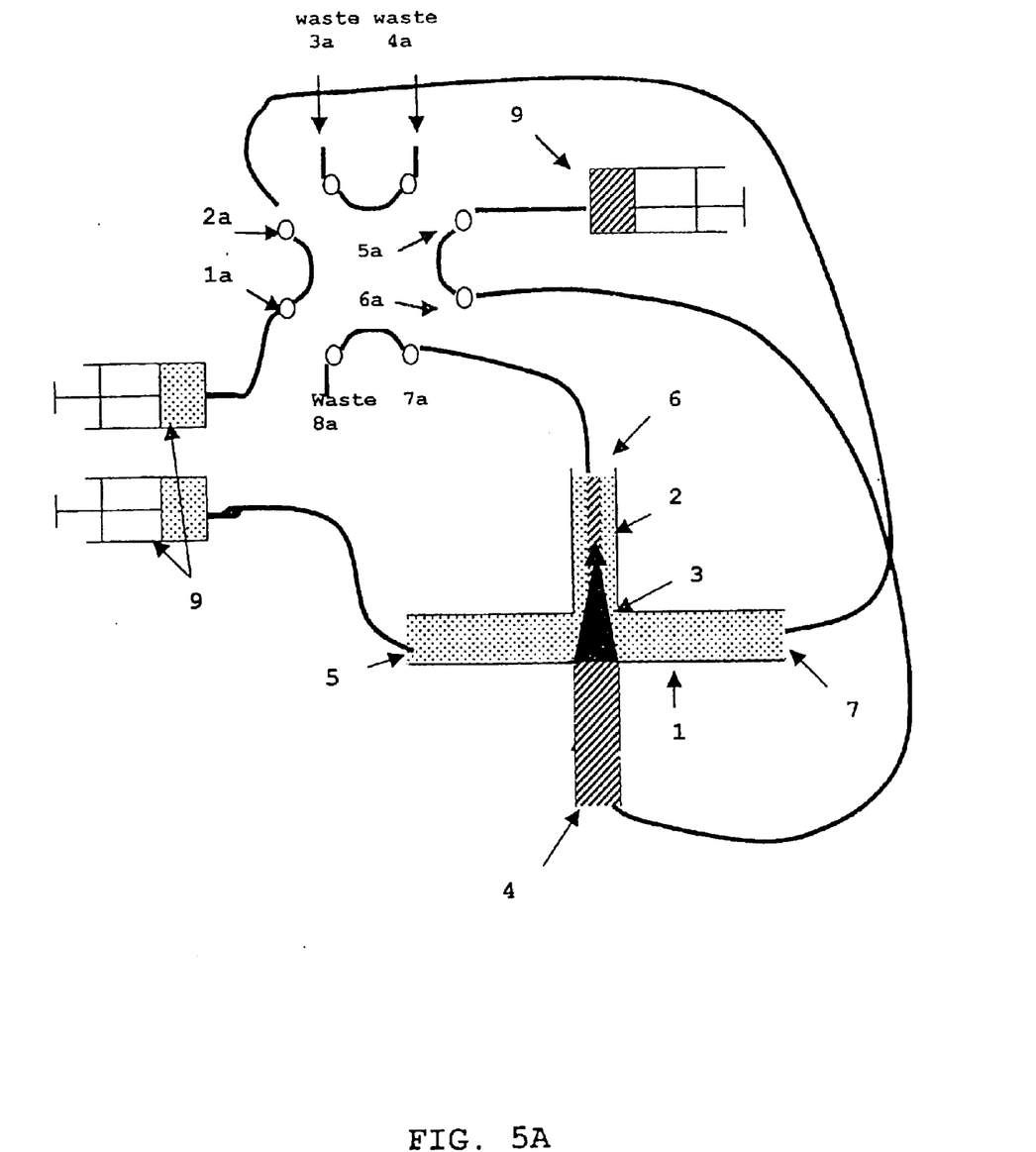
FIG. 5(a) shows a configuration of the pressure pinched injection.
Figure 5B:
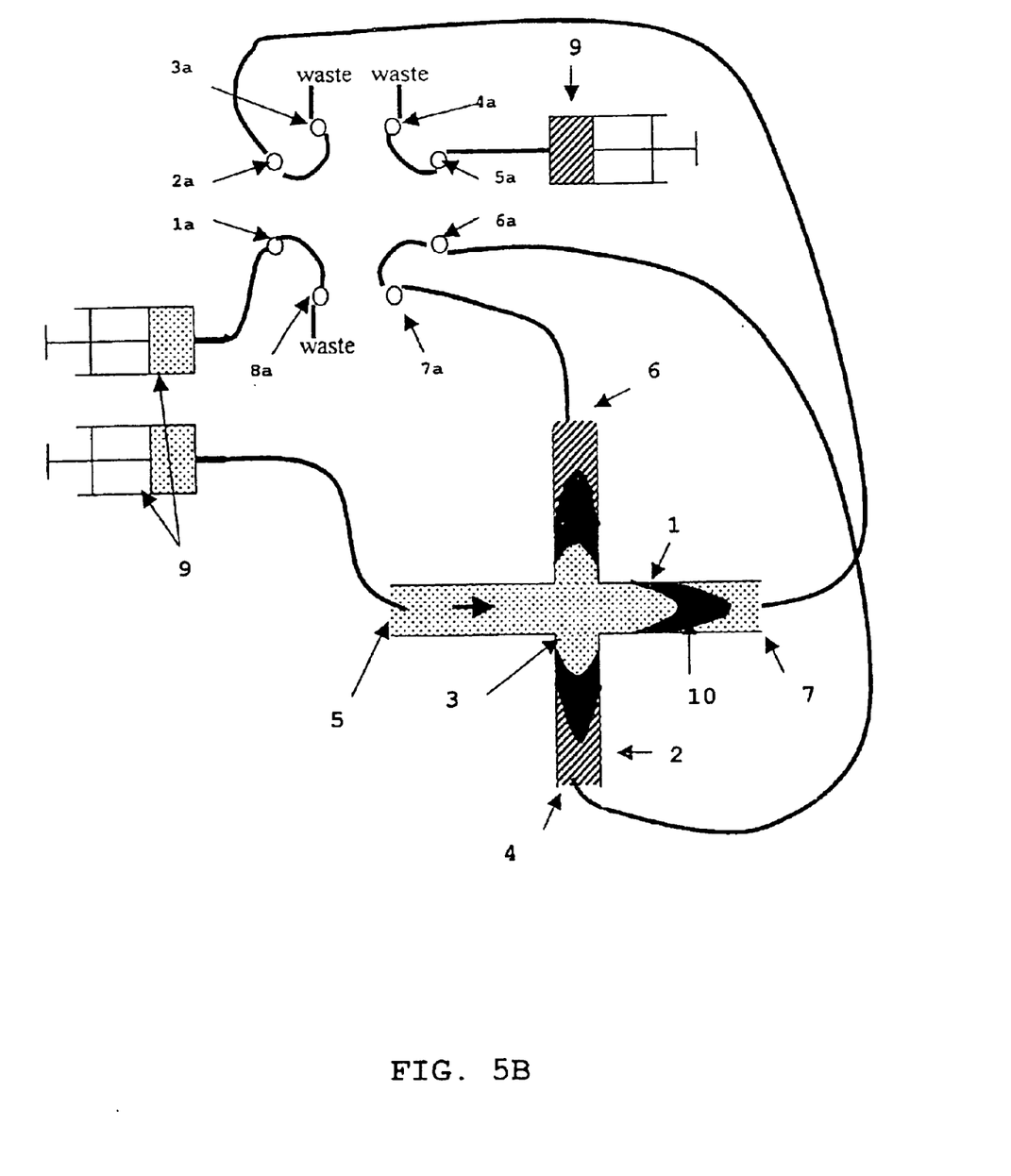
FIG. 5(b) shows a configuration of the separation position.

First, the running buffer must be connected directly to the structure, without going through the multi-port valve as presented in FIG. 5. This means that the same pressure is applied to an inlet formed by the opening at position 5 during the injection as well as during the separation. The other tubes are connected as presented in FIG. 5 (a), where a pressure is applied from three channel openings at positions 4, 5 and 7 towards the intersection 3 and where one single channel opening, at position 6, is connected to the waste. The pressure in the channels can be adjusted to get a symmetric or an asymmetric injection pattern that will generate a bigger or a smaller plug. In this regard the size of the syringes 9 can be the same or of different sizes in order to obtain a symmetrical or an asymmetrical triangle shape. When the multi-port valve is switched to the position shown in FIG. 5 (b), the running buffer direction is linear and brings a plug 10 with it through the main channel 1. The channel openings at positions 4 and 6 are connected together and therefore, the net flow in the second channel 2 is very low. Compression of the solution induces a push back effect in the second channel 2, allowing the injection of a small and very well defined plug 10. The solution is then pushed and the plug 10 transforms to a parabolic shape with respect to the flow rate. This type of injection is suited to any kind of solution and is not limited to the conductivity or surface properties of the material used for the structure.

EXAMPLE 4

Figure 6:
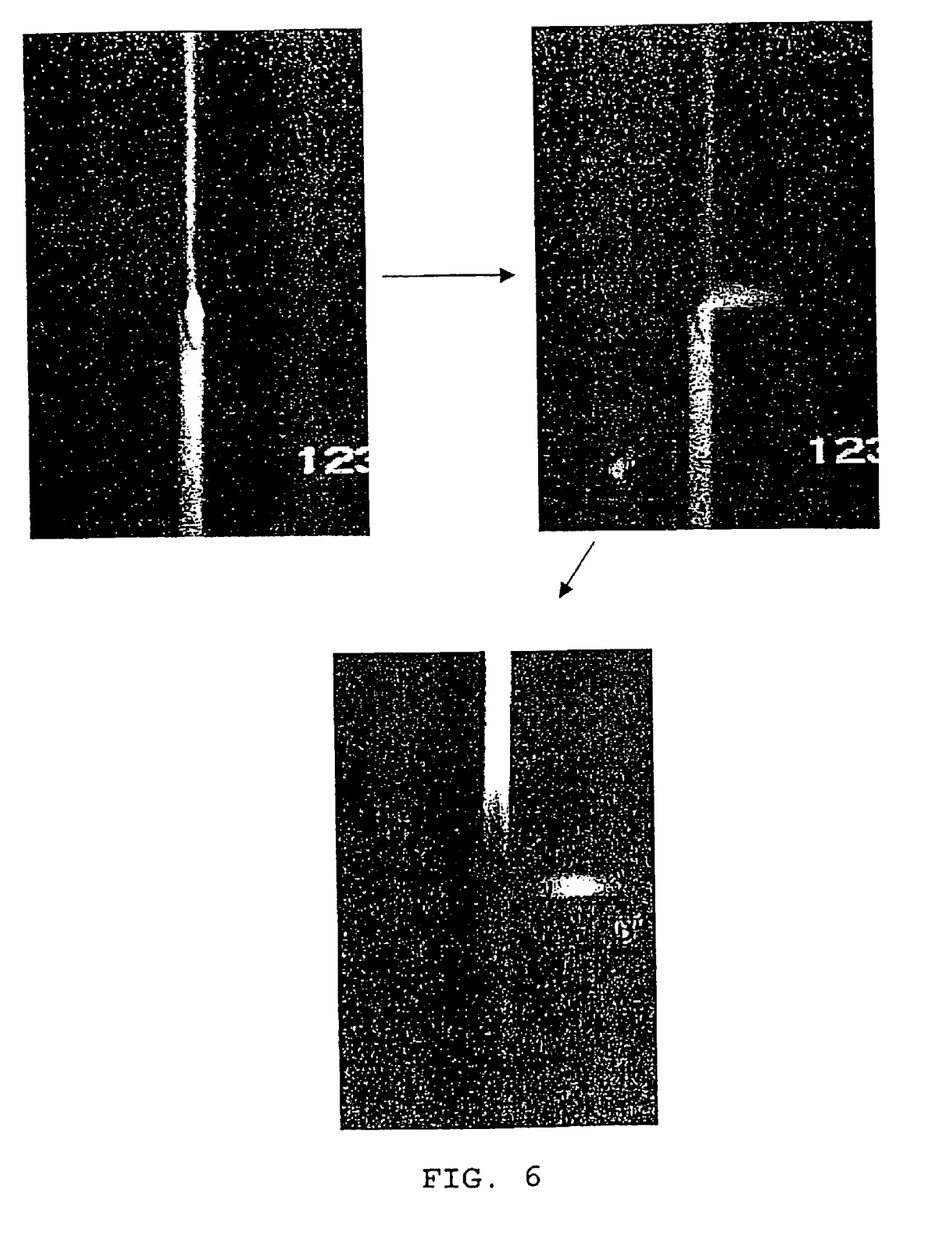
FIG. 6 is a photograph showing the fluorescent image of the intersection during pressure pumping under the configuration presented in FIG. 5(a)

In order to demonstrate the concept, the intersection of the channels was placed under a microscope and fluorescence and/or visible images were taken at different times during the injection or separation pattern. The picture presented in FIG. 6 clearly demonstrates the injection pattern shown in FIG. 5(a) when a fluorescent solution of 0.1 mM Fluorescein in 10 mM phosphate buffer at pH 7.4 was compressed between two side solutions that are not fluorescent.

Figure 7:
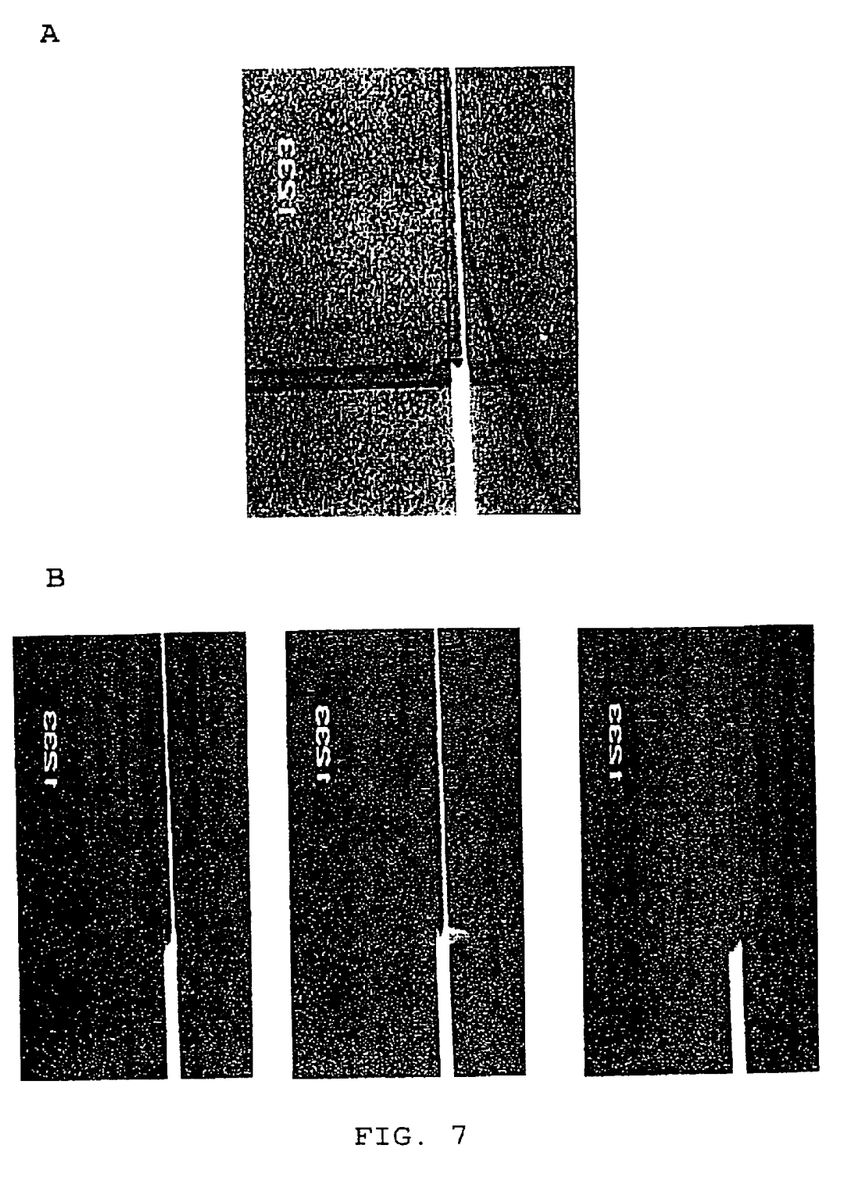
FIG. 7 is a sequence of photographs showing the position of the plug when injected into a channel as shown in FIG. 5(a) and when the device is then changed to the configuration shown in FIG. 5(b)

FIG. 7(a) corresponds to the configuration shown in FIG. 5(a) when the compression is not symmetrical, meaning that the flow rate is not equivalent in different channel sections. The sequence of images shown in FIG. 7(b) shows the behaviour of the flow at the intersection when the multi-port valve is switched from the position shown in FIG. 5(a) to that shown in 5(b). The plug 10 evolves in a parabolic shape and is then injected into the main channel 1 for separation.

EXAMPLE 5

Figure 8:
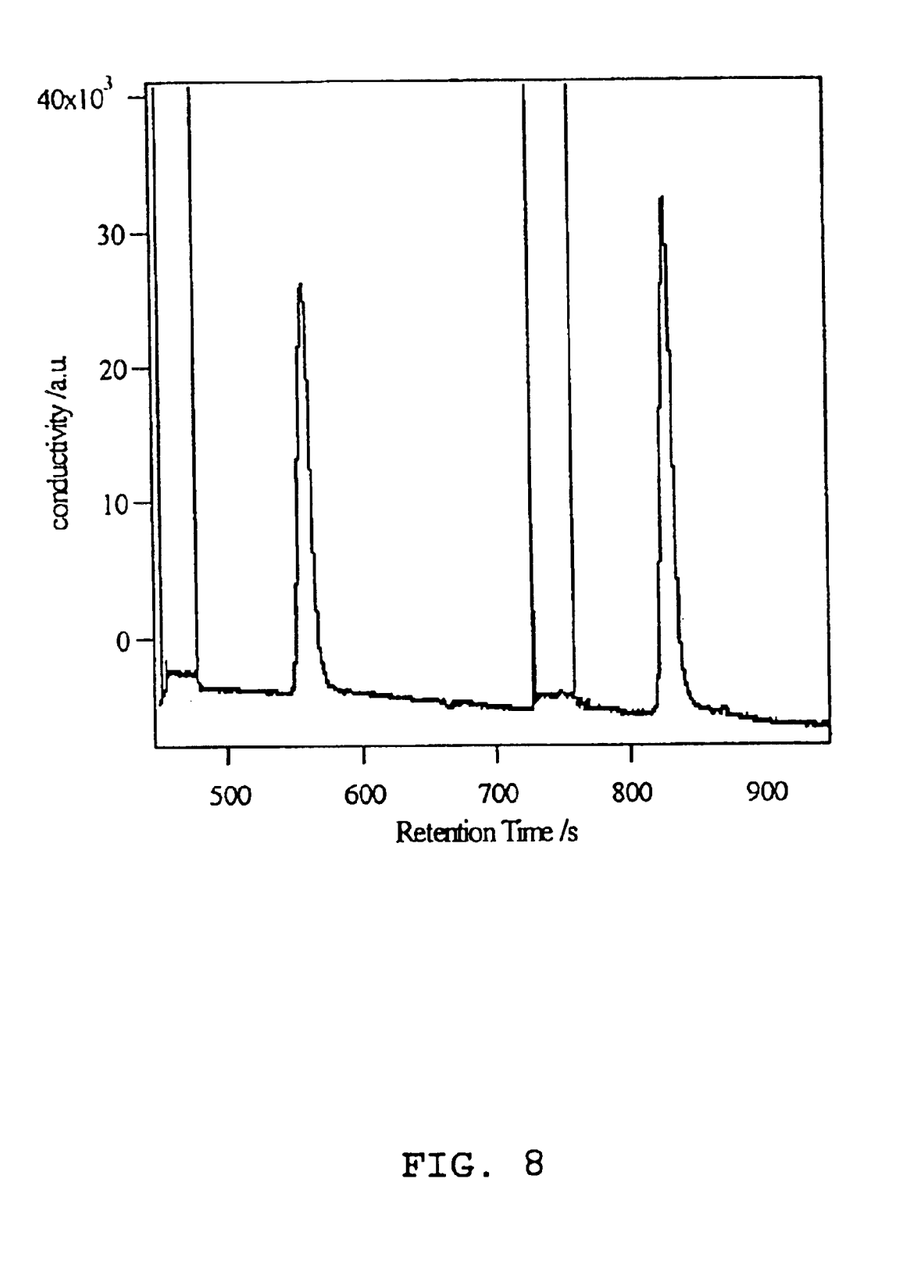
FIG. 8 is a chromatogram of the injected plugs in the configuration presented in FIG. 5.

To demonstrate the reproducibility of the two sequential injections shown in FIGS. 5a and 5b a solution of 10 mM Eosine B and 2 mM of sodium chloride was injected into the channel whilst the other flows were composed of pure water. Detection was performed by measuring the conductivity between electrodes inserted facing each other at the end of the channel. A chromatogram showing the results obtained is presented in FIG. 8.

The present injection pattern could be used with different solutions such as organic solvents, solutions containing salts or not containing salts as well as with a gradient elution prepared in the tubes. This is an important point when performing any kind of chromatography. This point is also a very important difference from the standard electrokinetic sample manipulations.

The device can also be arranged so that only the injection is sustained by pressure and that the separation is purely electrophoretic.

What is claimed is:

1. A micro-analytical apparatus for mechanically manipulating fluid samples, comprising:
a substrate having at least first and second covered channels, each having openings at opposite ends thereof, said first and second covered channels intersecting to form a common intersection with at least four arms;
wherein at least three of the openings of said first and second covered channels are connected to a multi-port valve to control the pressure in the channels, said multi-port valve having at least eight ports; and said multi-port valve being the sole actuator controlling the direction of flow of fluid samples in all the arms of said intersection, and controlling the directions of flow in all of said arms simultaneously; and
wherein said multi-port valve is switchable between:
a first position, wherein the multi-port valve provides a path for mechanical pumping of a first fluid through said multi-port valve in said first covered channel, while a first opening of said second covered channel is connected through said multi-port valve to mechanical pumping means and the second opening of said second covered channel is directly connected to mechanical pumping means so as to pinch said first fluid sample at said common intersection; and a second position where the openings of said first covered channel are connected through said multi-port valve so as to form a closed loop, while said first opening of said second covered channel is disconnected from any mechanical pumping means and the second opening of said second covered channel is directly connected to a mechanical pumping means so as to transport a second fluid in said second covered microchannel while maintaining constant pressure in both arms of said first channel.

2. A method of manipulating fluid samples using the apparatus of claim 1 comprising the steps of:

a. mechanically pumping an eluent solution into one end of the second covered channel and through the intersection while maintaining constant pressure between both end of the first covered channel when the multi-port valve is in a second position;

b. then switching the multi-port valve to the first position so that a sample solution is pumped into the first covered channel through an opening at one end thereof while pressure is applied at both ends of of the second covered channel so as to pinch said sample solution at the intersection; and c. switching the multi-port valve back to the second position so that the sample is pushed from the intersection along the second covered channel.

3. The method according to claim 2, wherein an electrical field is applied in a portion of said first or second covered channel in order to sustain or stop the flow of solution therein during the pushing of the sample along the second covered channel.

4. The method according to claim 2, wherein in step (c) the sample is pushed from the intersection along the second covered channel by means of electrophoresis or electroosmosis.

5. The method of claim 2, wherein at least part of the first or second covered channel contains a stationary phase in order to perform chromatography, electrochemistry, electrophoresis, immunological or enzymatic analysis or any combination thereof.

6. The apparatus of claim 1, wherein the substrate is made of a substance selected from the group consisting of glass, silicon, ceramics, organic polymers, metallic materials and mixtures thereof.

7. The apparatus of claim 1, wherein the channels in the substrate are covered by lamination, thermal bonding, anodic bonding, electrostatic interaction, pressure or a combination thereof.

8. The apparatus according to claim 1, wherein the first or second covered channel contains a detection region.

9. The apparatus according to claim 8, wherein the detection region consists of electrodes, or a window for spectroscopic detection.

10. The apparatus according to claim 1, wherein the first or second covered channel is connected to a detection device.

11. A micro-analytical apparatus for mechanically manipulating fluid samples, comprising:

a substrate having at least first and second covered channels, each having openings at opposite ends thereof, said first and second covered channels intersecting to form a common intersection with at least four arms;

wherein at least three of the openings of said first and second covered channels are connected to a multi-port valve to control the pressure in the channels, said multi-port valve having at least eight ports; and said multi-port valve being the sole actuator controlling the direction of flow of fluid samples in all the arms of said intersection, and controlling the directions of flow in all of said arms simultaneously; and wherein said multi-port valve is switchable between:

a first position, wherein the multi-port valve provides a path for mechanical pumping of a first fluid through said multi-port valve in said first covered channel, while the openings of said second covered channel are connected through said multi-port valve so as to form a closed loop; and a second position, wherein the openings of said first covered channel are connected through said multi-port valve so as to form a closed loop, while the multi-port valve provides a path for mechanical pumping of a second fluid through said multi-port valve in said second covered channel.

12. The apparatus of claim 11, wherein the substrate is made of a substance selected from the group consisting of glass, silicon, ceramics, organic polymers, metallic materials and mixtures thereof.

13. The apparatus of claim 11, wherein the channels in the substrate are covered by lamination, thermal bonding, anodic bonding, electrostatic interaction, pressure or a combination thereof.

14. The apparatus according to claim 11, wherein the first or second covered channel contains a detection region.

15. The apparatus according to claim 14, wherein the detection region consists of electrodes, or a window for spectroscopic detection.

16. The apparatus according to claim 11, wherein the first or second covered channel is connected to a detection device.

17. A method of manipulating fluid samples using the apparatus of claim 11 comprising the steps of:

a. mechanically pumping an eluent solution into one end of the first covered channel and through the intersection while maintaining constant pressure between both ends of the second covered channel when the multi-port valve is in a first position;

b. then switching the multi-port valve to a second position so that a sample solution is pumped into the second covered channel through an opening at one end thereof while maintaining constant pressure between both ends of the first covered channel; and switching the multi-port valve back to the first position so that the sample is pushed from the intersection along the first covered channel.

18. The method according to claim 17, wherein an electrical field is applied in a portion of said first or second covered channel in order to sustain or stop the flow of solution therein during the pushing of the sample along the first covered channel.

19. The method according to claim 17, wherein in step (c) the sample is pushed from the intersection along the first covered channel by means of electrophoresis or electroosmosis.

20. The method of claim 17, wherein at least part of the first or second covered channel contains a stationary phase in order to perform chromatography, electrochemistry, electrophoresis, immunological or enzymatic analysis or any combination thereof.

* * * * *

UNITED STATES PATENT AND TRADEMARK OFFICE
CERTIFICATE OF CORRECTION

PATENT NO. : 7,037,417 B2 Page 1 of 1
APPLICATION NO. : 09/812065
DATED : May 2, 2006
INVENTOR(S) : Joel S. Rossier et al.

It is certified that error appears in the above-identified patent and that said Letters Patent is hereby corrected as shown below:

Column 7:
In the claims, claim 2, line 21, "end" should read --ends--;

In the claims, claim 2, line 26, delete the second occurrence of "of".

Signed and Sealed this

Twenty-second Day of August, 2006

JON W. DUDAS
*Director of the United States Patent and Trademark Office*